United States Patent
Capaldo et al.

(10) Patent No.: US 7,371,590 B2
(45) Date of Patent: May 13, 2008

(54) INTEGRATED INSPECTION SYSTEM AND DEFECT CORRECTION METHOD

(75) Inventors: Kevin Patrick Capaldo, Mount Vernon, IN (US); Mark Allen Cheverton, Mechanicville, NY (US); Dennis Joseph Coyle, Clifton Park, NY (US); Michael John Davis, Mount Vernon, IN (US); Sameer Kirti Talsania, Evansville, IN (US); Masako Yamada, Niskayuna, NY (US); Chung-hei Yeung, Evansville, IN (US)

(73) Assignee: General Electric Company, Schenectady, NY (US)

( * ) Notice: Subject to any disclaimer, the term of this patent is extended or adjusted under 35 U.S.C. 154(b) by 345 days.

(21) Appl. No.: 11/285,331

(22) Filed: Nov. 21, 2005

(65) Prior Publication Data

US 2007/0117225 A1    May 24, 2007

(51) Int. Cl.
*H01L 21/66* (2006.01)
(52) U.S. Cl. ............................................. 438/14
(58) Field of Classification Search ......... 438/5–18; 356/239.1; 256/237.1
See application file for complete search history.

(56) References Cited

U.S. PATENT DOCUMENTS

| | | | |
|---|---|---|---|
| 4,938,601 A | 7/1990 | Weber | |
| 5,798,829 A | 8/1998 | Vaez-Iravani | |
| 6,379,868 B1 | 4/2002 | White | |
| 6,768,543 B1 | 7/2004 | Aiyer | |
| 6,922,236 B2 | 7/2005 | Vaez-Iravani et al. | |
| 2001/0013936 A1 | 8/2001 | Nielsen et al. | |
| 2002/0093648 A1 | 7/2002 | Nikoonahad et al. | |
| 2002/0114084 A1* | 8/2002 | Summersgill et al. | 359/742 |
| 2003/0011760 A1 | 1/2003 | Vaez-Iravani et al. | |
| 2003/0156280 A1 | 8/2003 | Reinhorn | |
| 2003/0227618 A1 | 12/2003 | Some | |
| 2004/0145734 A1 | 7/2004 | Shibata et al. | |
| 2006/0065645 A1* | 3/2006 | Nakasu et al. | 219/121.68 |
| 2006/0066845 A1* | 3/2006 | Capaldo et al. | 356/239.1 |

OTHER PUBLICATIONS

U.S. Appl. No. 11/285,332, filed Nov. 21, 2005, Harding et al., System and Method for Inspection of Films (Copy enclosed).
U.S. Appl. No. 11/285,329, filed Nov. 21, 2005, Capaldo et al., Method for Examining Molds and Apparatus for Accomplishing the Same (available in IFW).

(Continued)

*Primary Examiner*—Savitri Mulpuri
(74) *Attorney, Agent, or Firm*—Cantor Colburn LLP

(57) ABSTRACT

A system for the inspection of and a process for the correction of defects in a microreplicated optical display film manufacturing process. The process steps of manufacturing a master, a plurality of shims from the master, and a multiplicity of display films from each shim are integrated with a systemic defect identification and correction process. Each primary manufacturing step has its own inspection system and correction process where defect information for that step of the process is fed back and analyzed; and from that analysis the subprocess is adjusted to eliminate or reduce the detected defect. The systemic defect is identified as to its source and then fed back and analyzed in the correction step of the respective subprocess in order to cure the root of the defect.

16 Claims, 9 Drawing Sheets

OTHER PUBLICATIONS

U.S. Appl. No. 11/285,330, filed Nov. 21, 2005, Cheverton et al., Method for Detecting the Alignment of Films for Automated Defect Detection (available in IFW).

U.S. Appl. No. 11/285,137, filed Nov. 21, 2005, Yamada et al., Methods for Improving Mold Quality for Use in the Manufacture of Liquid Display Components (available in IFW).

* cited by examiner

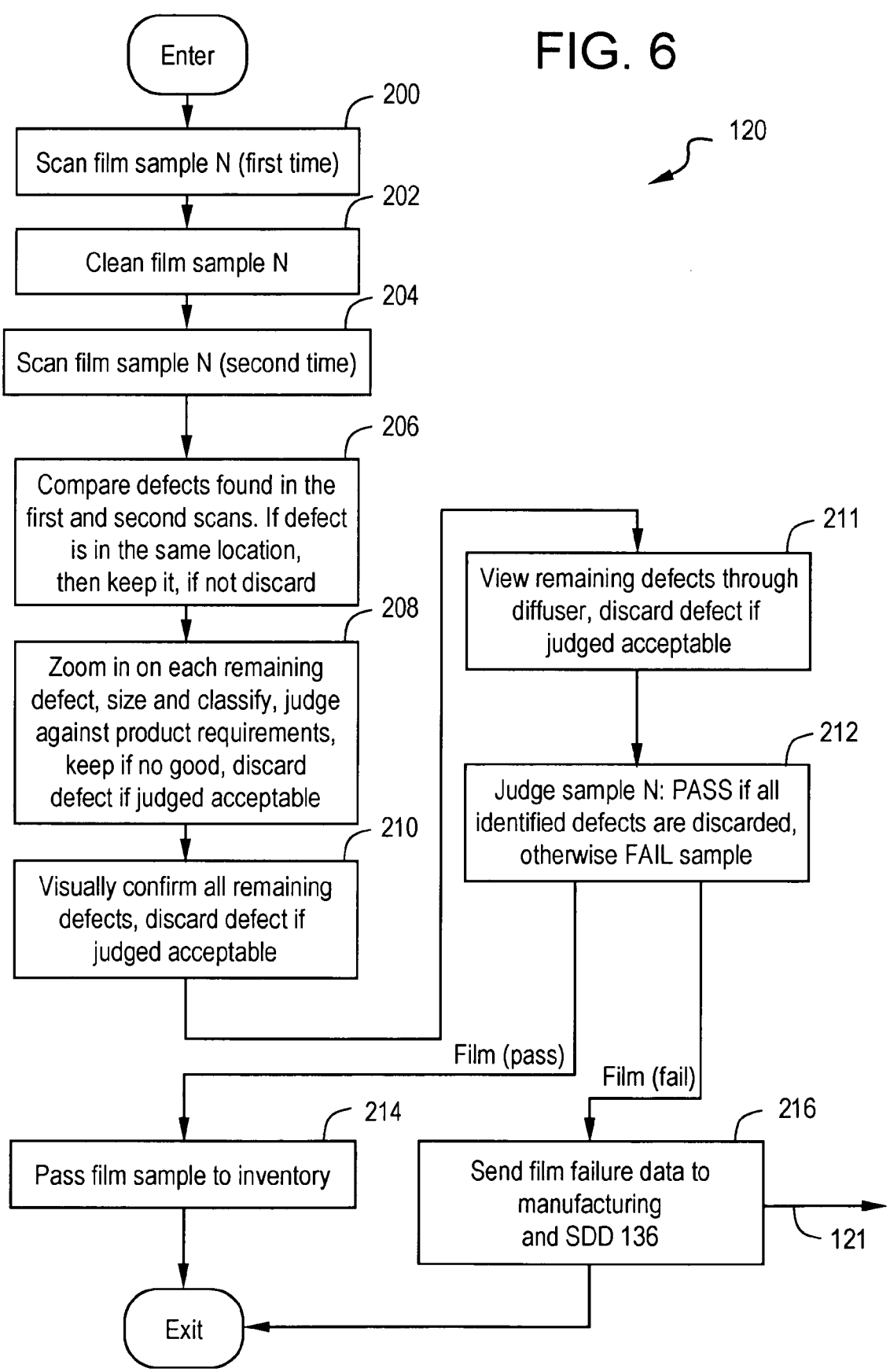

Table A
Coordinated Table of Defect results for M1-14-2

| Defect # | Position Machine Direction (In) | Position Cross Direction (In) | Shim Inspection Length (mm) | Shim Inspection Width (mm) | Visual Inspection Length (mm) | Visual Inspection Width (mm) | Type | Comment | Shim Camera Image | Film Camera Image |
|---|---|---|---|---|---|---|---|---|---|---|
| 2 | -8.7 | 6.2 | 0.60 | 0.10 | 0.40 | 0.05 | Dash | | | |
| 3 | -8.8 | 3.8 | 0.20 | 0.05 | 0.30 | 0.05 | Dash | | | |
| 5 | -10.9 | 9.8 | 0.25 | 0.10 | 0.40 | 0.10 | Dash | | | |
| 9 | -8.6 | 8.9 | 0.20 | 0.05 | 0.30 | 0.05 | Dash | Visible on Film - No Good | | |
| 11 | -4.2 | 5.7 | 0.08 | 0.05 | 0.20 | 0.10 | Smudge | | | |
| 14 | -1.3 | 2.8 | 0.30 | 0.10 | 0.40 | 0.10 | Dash | | | |
| 15 | -13.7 | 4.8 | 0.20 | 0.05 | 0.25 | 0.05 | Dash | | | |
| 16 | -13.6 | 8.3 | 0.30 | 0.20 | 0.40 | 0.10 | Dash | | | |

FIG. 7A

Table A (continued)
Coordinated Table of Defect results for M1-14-2

| Defect # | Position Machine Direction (In) | Position Cross Direction (In) | Shim Inspection Length (mm) | Shim Inspection Width (mm) | Visual Inspection Length (mm) | Visual Inspection Width (mm) | Type | Comment | Shim Camera Image | Film Camera Image |
|---|---|---|---|---|---|---|---|---|---|---|
| 17 | -12.7 | 4.5 | 0.30 | 0.08 | 0.30 | 0.05 | Dash | |  |  |
| 19 | -14.4 | 2.1 | 0.40 | 0.05 | 0.40 | 0.05 | Dash | Visible on Film – No Good |  |  |
| 20 | -16.4 | 2.3 | 0.30 | 0.10 | 0.40 | 0.05 | Dash | |  |  |
| 13 | -3.9 | 4.8 | 0.10 | 0.05 | 0.20 | 0.05 | Dash | Visible on Film - OK |  |  |
| 6 | -11.1 | 6.7 | 0.30 | 0.10 | | | Scratch | |  | 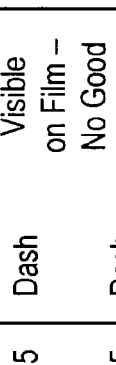 |
| 8 | -7.2 | 6.8 | 0.30 | 0.05 | Not Visible on Film | | Dash | Not Visible on Film | 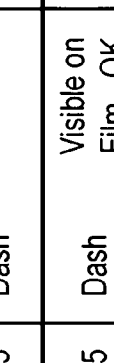 | None |
| 10 | -4.5 | 3.6 | 0.05 | 0.05 | | | Dot | | 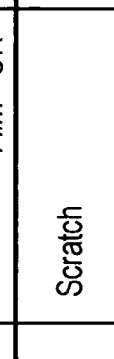 | 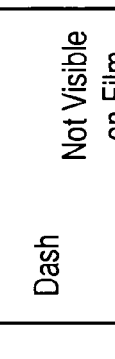 |
| 12 | -4.0 | 9.2 | 13.00 | 0.05 | | | Scratch | | 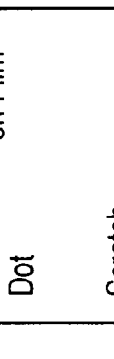 | None |

FIG. 7B

INTEGRATED INSPECTION SYSTEM AND DEFECT CORRECTION METHOD

BACKGROUND OF THE INVENTION

The invention relates generally to systems and methods for the inspection of manufacturing processes and, more particularly, is directed to an integrated inspection system and defect correction process for micro-replicated display film manufacture.

In backlight computer displays or other display systems, optical films are often used to direct light. For example, in backlight displays, light management films use prismatic structures (often referred to as microstructure) to direct light along a viewing axis (i.e., an axis substantially normal to the display). Directing the light enhances the brightness of the display viewed by a user and allows the system to consume less power in creating a desired level of on-axis illumination. Films for turning or directing light can also be used in a wide range of other optical designs, such as projection displays, traffic signals, and illuminated signs. The prismatic structures are generally formed in a display film by replicating a metal tool, mold, or electroform having prismatic structures disposed thereon, via processes such as stamping, molding, embossing, or UV-curing. It is generally desirable for the display film and the mold to be free from defects so as to facilitate a uniform luminance of light. Because such structures serve to strongly enhance the brightness of a display, any defects, even if they are small (on the order of 10 microns), can result in either a very bright or very dark spot on the display, which is undesirable. The mold and the display films are therefore inspected to eliminate defects.

Molds, for example, electroforms are generally used for manufacturing light management films, such as prism sheets, for use in liquid crystalline displays. In general, such light management films have at least one microstructured surface that refracts light in a specific way to enhance the light output of the display. Since these films serve an optical function, the surface features must be of high quality with no roughness or other defects. This microstructure is first generated on a master, which may be a silicon wafer, glass plate, metal drum, or such; and is created by one of a variety of processes such as photolithography, etching, ruling, diamond turning, or others. Since this master tends to be expensive to produce and fragile in nature, tooling or molds are typically reproduced off of this master, which in turn serve as the molds from which plastic microstructured films are mass-produced. These tools can be metal copies grown via electroforming processes, or plastic copies formed via molding-type processes. Tools copied directly from the master are called $1^{st}$-generation, copies of these tools are called $2^{nd}$-generation, etc. In general, multiple copies can be made of every tool made at any generation, leading to a geometric growth in number of tools with each generation—i.e. a "tooling tree" is produced. Each generation is an inverted image of the previous generation. If the desired final product is a "positive" geometry, then any generation of tooling that is a negative can be used as a mass-production replication tool. If the master is manufactured as a negative, then any even-generation mold can be used for mass-production.

One difficulty always present when a manufacturing process, such as the optical display film manufacturing process, uses a component or subprocess in a subsequent step of the process is the systemic defect. If a major component, such as a shim tool or a master tool, is defective, then every subsequent mold and film replicated from those components will be defective. In prior attempts to alleviate this problem, the optical display film manufacturing process has been separated into three semi-independent manufacturing processes, the master tool, the shim tool and the display film manufacturing processes. Each primary manufacturing process has had an independent inspection and defect correction process that identifies a defective component or product at that particular step in the process and then removes it from the process chain. These processes are intended to prevent a defective master tool from being made into a defective shim tool, a defective shim tool from being made into defective film samples, and defective film samples from being sold.

However, not all the defects that will eventually make defective film are found in the inspection and defect correction processes of the master tool and the shim tool manufacture. Also the master and the shim tools eventually wear out and have to be replaced and some defective or questionably defective display film may enter the production chain before the defect is identified and corrective action taken. Most notably, in the step of the process at which systemic defects are best identified, the film inspection process, it is very difficult to collect sufficient and relevant data with human inspectors and prohibitive to fully inspect every product unit.

Therefore, there is a need to be able to better identify systemic defects in the manufacturing process for optical display films and to advantageously use such systemic defect information to correct the process in earlier steps so as identify the root cause of those defects. Such integration of the systemic defect information with corrective actions in one or all of the primary process steps will assist in eliminating or reducing the possibility of such defects in the future.

Further, the prior inspection systems and defect correction processes of the manufacturing process for microreplicated films have some disadvantages that need to be overcome. Industry practice presently involves intensive human visual inspection in order to control the quality of microreplicated optical display films. Human inspectors are very good at determining the classification of a defect, even across a complex decision matrix of defects that are objectionable within an LCD display. They, however, are not very fast at scanning and identifying many possible defects across large numbers of products for later classification and decision.

Moreover, there tends to be at the possible defect identification stage more of a subjective determination with many human inspectors collecting a large amount of data. One of the more important data for defect correction in the microreplicated optical film process is the location of a defect, as many defects across the products in a similar or the same location would tend to show a systemic defect such as a defective master or shim tool. Reliance on human inspectors makes data collection of defect position information difficult because such details require extra time in an already costly inspection process.

Because the primary useful characteristics, and thus defects, of the display film are optical, the inspection processes of these products tend to lend themselves to automated or machine vision systems. However, the use of machine vision systems have not generally been accepted in the LCD backlight industry as a superior method for quality control due to its limited flexibility in detecting the wide range of optical defects that are objectionable in an LCD display film. Machine vision systems are very efficient at making initial inspections and identifying many possible defects over many products by rapidly scanning and storing data about such defects including their location. These automated inspections can also be made by a machine vision system that has the advantage of operating without stopping production.

Therefore, there is a need to coordinate and integrate the machine vision systems and human inspections in the manufacturing of optical display film in order to use their individual strengths to advantage. This would produce a synergistic effect and provide an improved quality control process for the optical display manufacturing process whereby large numbers of product can be easily and quickly scanned to identify defects and then have actual defects classified visually in an accurate manner.

With recent improvements to machine vision systems, including multiple resolution systems where rapid scans at low resolutions can be made to locate possible areas of interest and then slower scans of the identified areas at higher resolution can be made to classify such areas, these tools should become even more practical in optical display film inspection process. There is, however, substantial difficulty in setting the machine vision system operating parameters in any given manufacturing process, particularly for an optimum scan speed and resolution. Each manufacturing process has its own particular set of defects that it is trying to capture and there is always a trade off between manufacturing efficiency and quality.

Therefore, there is a need to provide a method for more accurately controlling the operating parameters and classification rules of a machine vision system in the display film manufacturing process to reduce the number of false positive defects for efficiency sake while accurately classifying most or all of actual defects for quality sake.

SUMMARY OF THE INVENTION

The novel technique provides a system and method for improving the quality of microreplicated optical display films and the efficiency by which they are manufactured.

An inspection system is utilized in the manufacture of microreplicated optical display films where preferably a master tool is first manufactured and then used to replicate a plurality of shim tools by electroforming, each of which are in turn utilized to replicate a multiplicity of display film elements in plastic. After manufacture, the display film elements are inventoried until they are sold. To aid the defect correction process of the inspection system and to assist in overall manufacturing and inventory control, each of the display films or batch of display films contain an identifier that can be traced back to the shim tool from which it was made. Similarly, each shim tool has an identifier that can be traced back to the master tool from which it was made.

Preferably, each of the three primary manufacturing processes has an inspection system and defect correction process where one or more of the manufactured products (films) or sub-products (masters, shims) are inspected and either passed on to the next part of the manufacturing process chain or are failed and removed from further steps in the process. The failure information obtained from each of the inspection processes is also analyzed at each primary process step and fed back in a correction step to adjust the particular process so as to eliminate or at least significantly reduce similar failures in the future.

Therefore, the system comprises an inspection system with a correction procedure advantageously based upon feedback from the inspections of the product at every process steps. This allows the manufacturing system to efficiently track defects back to their source in the overall manufacturing process and allows corrective action that will eliminate the root causes of such defects.

According to another aspect of the invention, the inspection system additionally includes a systemic defect detection process that inspects either a subproduct or the final product of the manufacturing chain and analyzes the systemic defects to determine whether such defects are caused by one or more of the primary process steps, i.e. the film manufacturing process, the shim tool manufacturing process, or the master tool manufacturing process. Once the cause of a systemic defect has been determined, the information about the systemic defect is fed back to the appropriate manufacturing process step and analyzed so that that particular part of the process can be adjusted appropriately to eliminate or at least reduce the probability of the defect occurring in the future. This feedback of systemic defects, in addition to the inspection of products and correction of defects at each process step, produces a cumulative benefit in increased efficiency and quality in the display film manufacturing process.

Another aspect of the invention includes an identification system for the product so that when display film units are in inventory or finished with the manufacturing process their origin and location remain known. For example, each display film sample is identified as to the shim tool from which it was made and each shim tool is likewise identified as to the master tool from which it was made. In this manner, when a defective shim or master tool is identified, the display film products made with the defective starting component, and all intermediate products can be removed from the manufacturing process or inventory. In an adaptation of this aspect of the invention, the correction process also provides a process for determining when a defect emerged with respect to either a shim or a master tool. This permits only those units of the product known to be unacceptable to be removed from the market.

According to another aspect of the invention, the inspection system includes at least one machine vision system for a primary manufacturing step having classification rules, and at least multiple resolutions and scan speeds as controllable operating parameters. In an advantageous method, the machine vision system under an initial setting for its operating parameters first scans the subproduct or product, for example a shim tool, and stores the classification characteristics for the defects found. It labels the defects according to their probability of being actual defects under several categories such as likely (very high probability), probable (high probability), possible (medium probability), and unlikely (low probability). The product failure information for products or further subproducts made with or related to the subproduct or product of the manufacturing step is fed back to that manufacturing step, for example, the film failure information generated by the display film manufactured from a particular shim tool. Optionally, this may be in addition to or as an alternative to the systemic defect information utilized as feed back.

This subsequent related defect information is then compared to the defect information stored for the particular shim tool. The comparison will produce a reclassification of those false positive defect characterizations from the machine vision system to unlikely where there are no matching defects in the subsequent product. The comparison will also produce a reclassification of those false negative defect characterizations by the machine vision system to likely by a confirmation that the defects that were only possible or probable subsequently appear as actual defects in the subsequent product. In response to an classification upgrade of certain stored defects to likely, or a classification downgrade of certain stored defects to unlikely, the machine vision system operating parameters and classification rules are modified to have similar features correctly classified in the future.

According to yet another aspect of the invention, the inspection system includes at least one automated machine vision system inspection step integrated with a visual inspection step for a primary manufacturing process. Preferably, the inspection process is used for the inspection of display film where there are large numbers of samples to be inspected and where efficiency and quality are important. In a first step of the method, the machine vision system uses a low resolution high speed scan to identify possible defects in a display film sample. The display film is then cleaned and scanned a second time with the results of the two scans compared. Those defects having the same location on both scans are declared as possible defects and the rest are discarded as dust or removable defects. The resolution of the machine vision system is then increased and then each defect is rescanned. Each defect is then classified according to a set of classification rules and the acceptable possible defects then discarded. A table of the remaining defects classifying them as to size, location and type is given to a human inspector for visual examination. Based upon the visual examination and classification rules for the visual examination the human inspector will either eliminate all the defects in the table as acceptable and pass the film display sample or will preliminarily fail the display film sample. Because the display film is meant to be used with a diffuser, the human inspector will view the preliminarily failed display film sample together with a diffuser to test whether this will eliminate all remaining visual defects. If all defects are eliminated, then the display film is passed to inventory. Otherwise the display film sample is failed.

DESCRIPTION OF THE DRAWINGS

These and other features, aspects, and advantages of the present invention will become better understood when the following detailed description is read with reference to the accompanying figures, wherein:

FIG. 6 is a detailed system flow diagram of the process steps for inspecting display film samples as illustrated in FIG. 4;

FIGS. 7A and 7B are a tabular diagram, including pictorial representations of defect information, correlating the defect information of a shim tool gathered with a machine vision system with the defect information of a display film sample made with that shim tool and gathered by an integrated machine vision system and visual inspection system.

DETAILED DESCRIPTION OF THE EMBODIMENTS

The following detailed description will use as an example a micro-replication manufacturing process for making a multiplicity of display films from one or more tools (shims) that have been made from a master. However, it will be evident that the invention may be used in support of any number of differing manufacturing processes where sub-products (including molds or tools), or sub-processes (including a result), from one step in a sequence of a process steps are used to make further sub-products that can then be incorporated into or used in making the finished products.

The manufacturing system for display film including an automated inspection system and defect correction procedure will now be more fully described with reference to the generalized system block diagram illustrated in FIG. 1. In that figure and in more detail in FIG. 2, the manufacturing and inspection process of the master is shown as Step 110 and includes the commonly known steps using the process procedures, parameters, and equipment suitable for the process. Preferably, the manufacturing process for the master includes forming a metal drum or plate that is relief machined with a desired texture on its surface. The texture may be in the form of prisms that refract light.

After each master is manufactured in Step 111, it is inspected in Step 112 to determine whether it is acceptable to make shim tools from. If the master is acceptable, then it is passed on to the shim tool manufacturing in Step 114. If the master does not pass the tests set out for it in Step 112, then it is failed and information on its failure passed to step 126 where the process conditions and procedures related to the failure are analyzed to determine the cause. Preferably, the inspection process of the master is visual, but optionally could be performed by a machine vision system. If a cause can be determined, the master manufacturing process is then adjusted in Step 124 to change the process conditions or procedures necessary to reduce or eliminate the risk of similar failures in the future.

Figure 1:
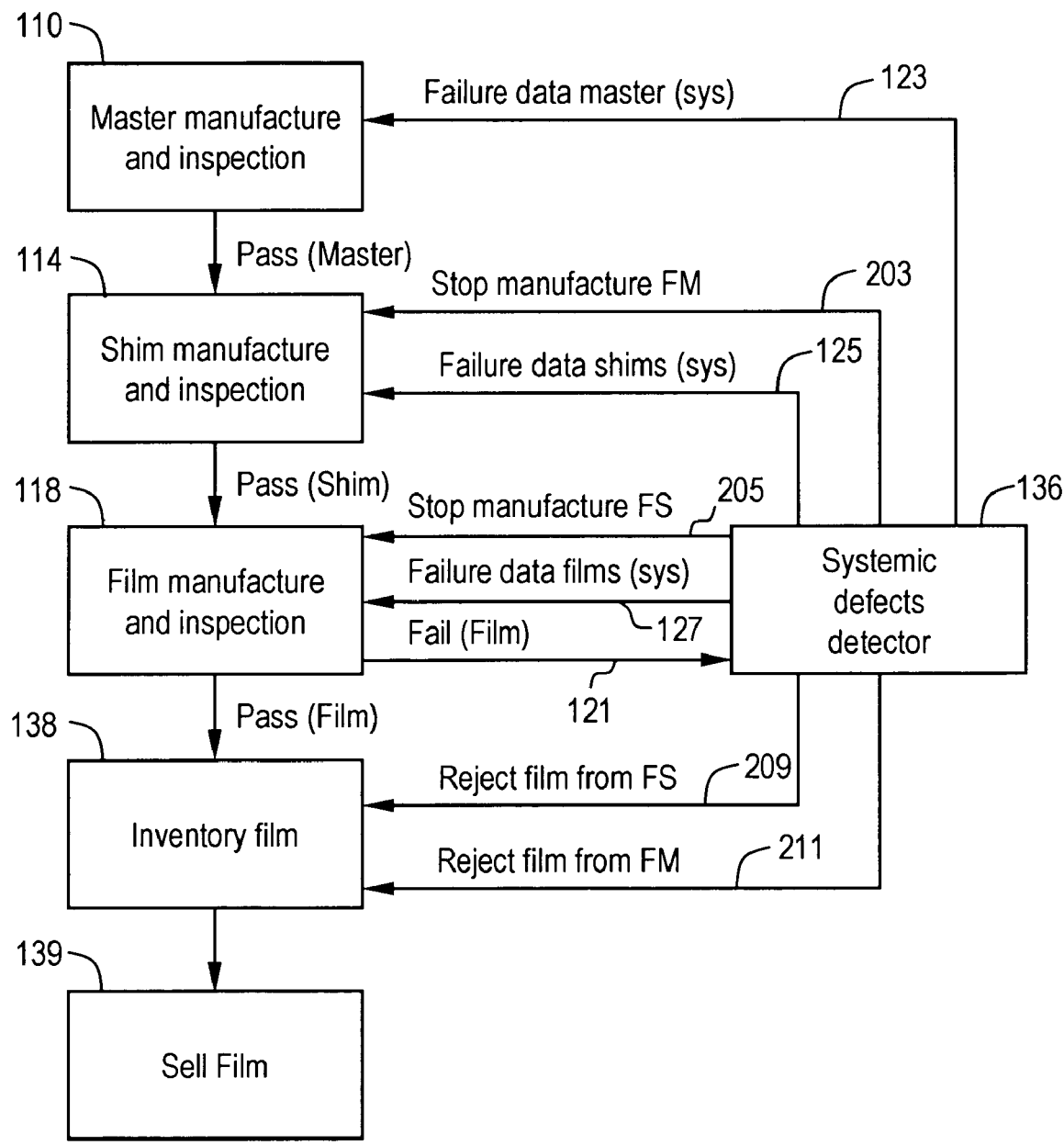
FIG. 1 is a detailed system block diagram of a microreplicated display film manufacturing process incorporating the invention.
Figure 2:
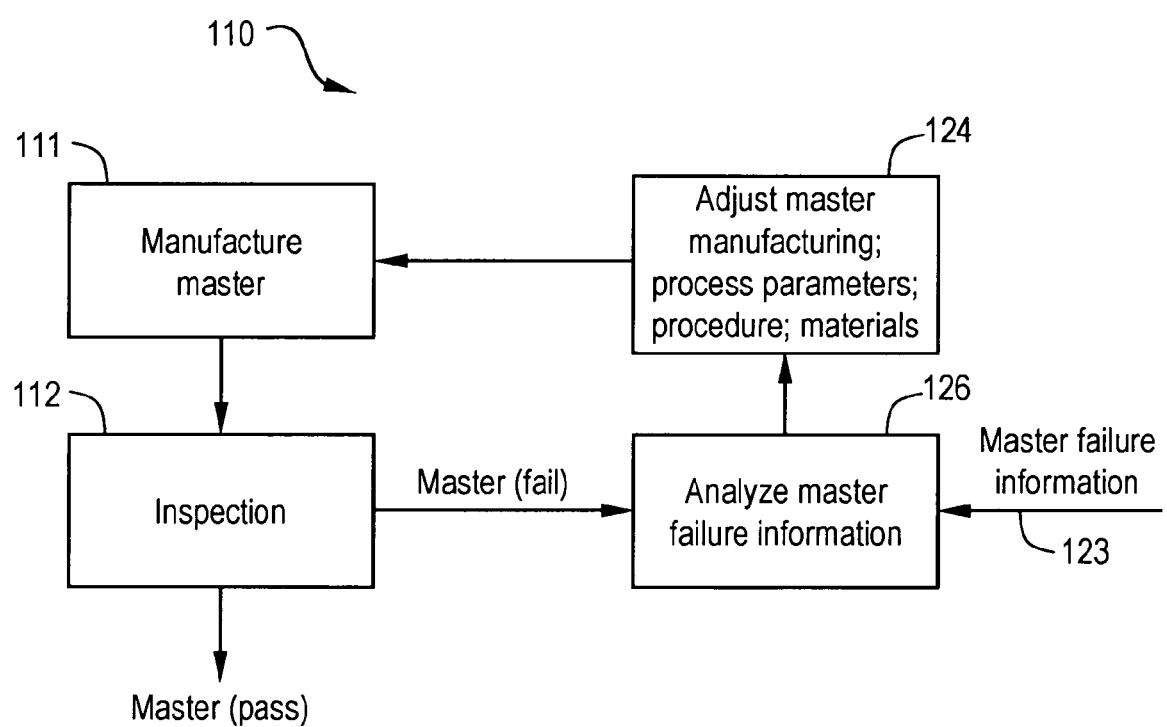
FIG. 2 is an expanded system block diagram of the master tool manufacturing and inspection process steps illustrated in FIG. 1.
Figure 3:
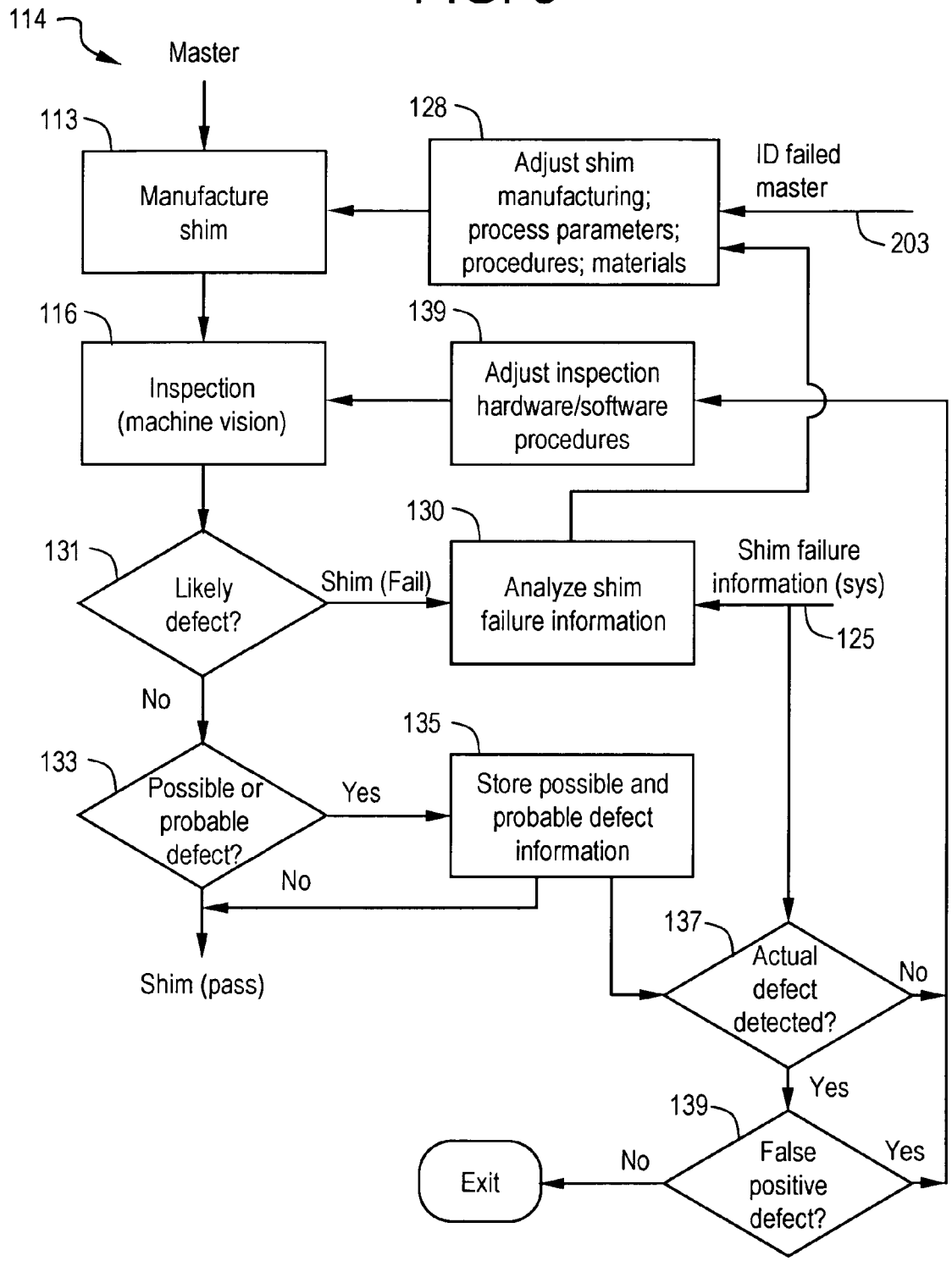
FIG. 3 is an expanded system block diagram of the shim tool manufacturing and inspection process steps illustrated in FIG. 1.

Similarly, the manufacturing and inspection process of a plurality of shim tools from a single master is shown as Step 114 in FIG. 1 and in more detail in FIG. 3. The manufacturing step 113 of a shim includes the commonly known steps using the process procedures, parameters, and equipment suitable for the process. Preferably, each shim tool is electroplated on the surface of the master and then peeled off as an electroformed tool. The shim or plate tool has the same surface texture that was machined in the surface of the master, in the preferred illustration refractive prisms. Alternatively, the tool being copied may be one of the shim tools that is first machined or formed with the desired textured surface. The manufacture of additional shim tools can then be by the electroplating replication described or some different surface transfer process.

After each shim tool is manufactured, it is inspected in Step 116 to determine whether it is acceptable to make display films from. If the shim tool is acceptable, then it is passed on to the display film manufacturing in Step 118. If the shim tool does not pass the tests set out for it in Step 116, then it is failed and information on its failure passed to step 130 where the process conditions and procedures related to the failure are analyzed to determine the cause. If a cause can be determined, the shim manufacturing process is then adjusted in step 128 to change the process conditions, procedures, materials or equipment necessary to reduce or eliminate the risk of similar failures in the future.

Optionally, as an improvement to the inspection system and correction procedure, the shim inspection Step 116 also includes a machine vision system and an adjustment Step 139 for the machine vision system. The adjustment process is provided to the inspection process and more particularly to the machine vision system where systemic shim failure information is fed back and analyzed in the process to increase the accuracy and efficiency of the machine vision inspection equipment. As previously noted, the inspection Step 116 identifies and classifies the defects in shim tools from the shim manufacturing Step 113.

When the inspection system includes a machine vision system the operating parameters of the system need to be chosen. Several important parameters are the resolution and speed of a machine vision scan and the logic rules for the identification and classification of defects. In the optional process, the identification and classifications rules, resolution and scan speed of the machine vision system are set to identify and classify likely, probable, possible and likely defects, rated as to the probability of their being actual defects. Likely defects have a very high probability of being actual defects and unlikely defects have a very low probability of being actual defects. One skilled in the art would conventionally know how to objectively set these seemingly subjective criteria, for example, by statistical or historical data, fuzzy logic, heuristics or the like.

When the defect inspection system identifies a defect as likely in Step 131, it will fail the shim tool under inspection and transfer the information on the failure to Step 130 for analysis and possible correction of the shim manufacturing process as before. For possible or probable defects, as tested for by Step 133, the shim tool will be passed on to manufacturing as before while the probable and possible defect information will be stored in Step 135 before the process continues. The shim tool with probable or possible defects is essentially on probation and the inspection system will wait for feedback from the film manufacturing process before deciding whether to fail the shim tool or not. Those shim tools with no defects or unlikely defects are passed on to the film manufacturing Step 118.

Upon the receipt of shim failure information from the systemic defect identification process step, the process in addition to adjusting the shim manufacturing process as previously disclosed in Steps 128, 130 also compares those noted effects against the possible and probable shim tool defects which have been stored. If an actual shim tool defect has been identified through the systemic defect identification process and the vision system inspection 116 only labeled it probable or possible for that shim (or shims), then in Step 139 at least one of the operating parameters of the machine vision system or the identification and classification rules is adjusted to cure that deficiency or at least increase the probability that such future defects will be labeled likely. Similarly, a shim tool defect that has not been confirmed through the systemic defect identification process and the vision system inspection 116 labeled a defect probable or possible for that shim (or shims), then in Step 139 at least one of the operating parameters of the machine vision system or the identification and classification rules is adjusted to cure that deficiency or at least increase the probability that such future defects will be labeled unlikely. Optionally, the actual film failure information for those display films that are made from shim tools having possible or probable defects can be fed back to decision nodes 137 and 139 for such corrective purposes.

Figure 4:
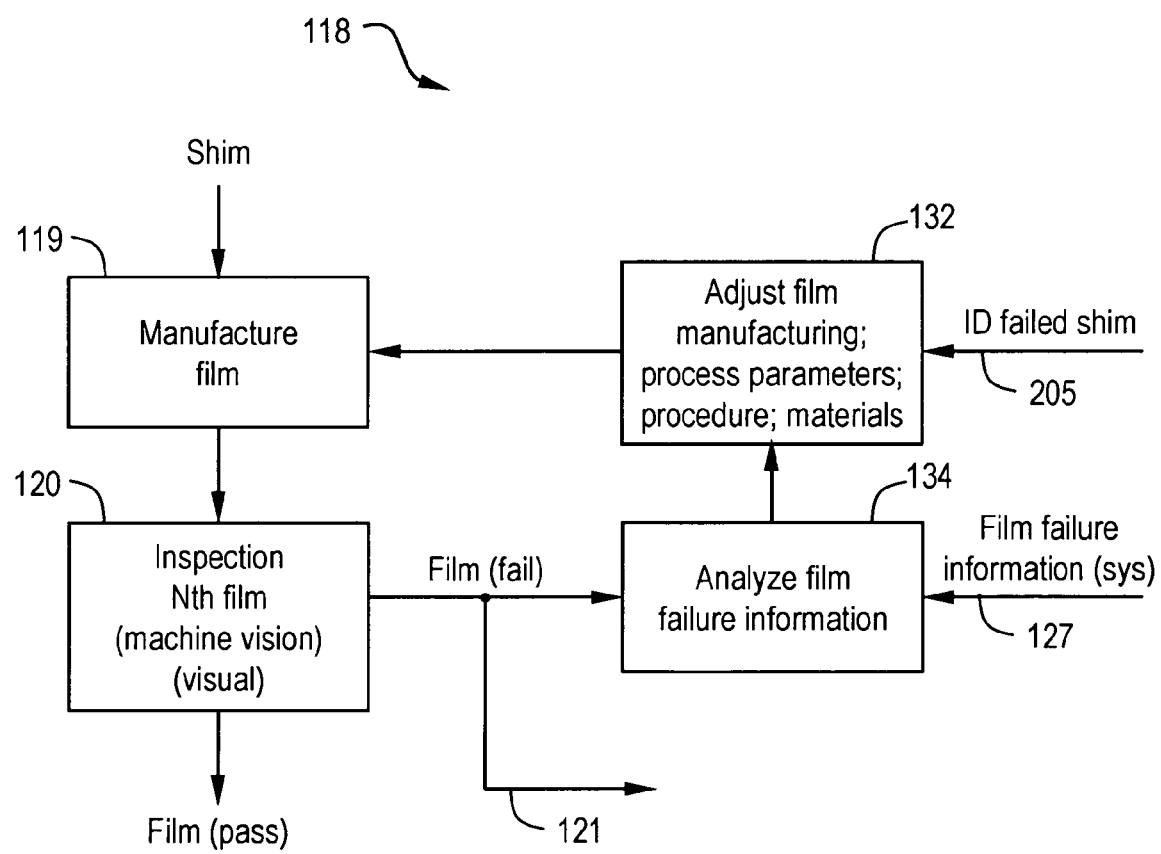
FIG. 4 is an expanded system block diagram of the display film manufacturing and inspection process steps illustrated in FIG. 1.

The manufacturing and inspection process of a multiplicity of films Y from each shim tool is shown as Step 118 in FIG. 1 and in more detail in FIG. 4. The manufacturing step 119 includes the commonly known steps using the process procedures, parameters, and equipment suitable for the process. Preferably, an electroformed shim tool, either from a master or from another shim tool, is used in a high-speed mass-replication process that transfers this microstructure into a plastic film via embossing, molding, UV-curing, or the like.

While a large number of display films are being manufactured from one or more shim tools, every Nth one is inspected in Step 120 to determine whether it is acceptable. The inspection process for the display film manufacture is preferably a machine vision system inspection integrated with a visual inspection by human inspector. If the film does not pass the tests set out for it in Step 120, then it is failed and information on its failure passed to step 134 where the process conditions and procedures related to the failure are analyzed to determine the cause. If a cause can be determined, the manufacturing process is then adjusted in step 132 to change the process conditions or procedures necessary to reduce or eliminate the risk of similar failures in the future.

Film that is manufactured in Step 119 and passes inspection in Step 120 is placed in an inventory in Step 138 before being sold in Step 139. The inventory in Step 138 will include many films that have not been inspected and those display film samples that have been inspected and have passed the inspection. Further, all films throughout the process are identified as to heritage, for example, the shim from which a film was made is associated with its inventory number and the master from which the shim was made is also associated with such film.

This describes suitable inspection system and defect correction processes where every sub-product in the process is inspected and the respective process step corrected based on the results of the inspection. However, there may still be defects in the master or shim tools which went undetected and which can cause a great deal of display film scrap if they are allowed to continue and if not detected and corrected early in the manufacturing cycle. The invention provides an integrated inspection system where the defects in the final product are also inspected for common or recurring defects which could be caused by defective sub-products made earlier in the manufacturing process chain. Such systemic defects are then used as feedback to further fine-tune the primary steps of the manufacturing process.

Returning to FIG. 1, in Step 136 the inspection system and defect correction process receives the film failure information for the process in Step 118 via data path 121 and detects whether a systemic defect is occurring in the overall manufacturing process. A further determination will then be made as to which part of the manufacturing process caused the systemic defect. If the defect was caused by the film-manufacturing step 119 of the process, then an analysis of the film failure information fed back via data path 127 to Step 118 is begun to adjust the film manufacturing process to eliminate or lessen the likelihood of such defect continuing to occur. In a similar manner, if the defect was caused by the shim-manufacturing Step 113 of the process, then an analysis of shim failure information fed back via data path 125 to Step 114 is begun to adjust the shim manufacturing process to eliminate or lessen the likelihood of such defect continuing to occur. Alternatively, if the defect was caused by the master-manufacturing Step 111 of the process, then an analysis of master failure information fed back via data path 123 to Step 110 is begun to adjust the master manufacturing process to eliminate or lessen the likelihood of such defect continuing to occur.

Once a systemic defect has been identified, it is also imperative to minimize the impact on the total manufacturing system. This is accomplished not only by correcting the individual process steps as described above so that more defects are not generated, but also by eliminating from inventory those products that are likely to be defective and incorporate the systemic defect. Further, those sub-products and their progeny that are labeled defective should be removed from the active or manufacturing part of the process. In the inspection system and defect correction process shown in the figure, this is accomplished by sending the identification of the any failed master from Step 136 to Step 114 via data path so that the master can be removed from the manufacturing process for shims. Additionally, this is accomplished by sending the identification of the any failed shim tool from Step 136 to Step 118 via data path 205 so that it can be removed from the active manufacturing process for display films. Step 136 also sends the identification of any failed master or shim tool and when it failed via data paths 209, 211 to the inventory in Step 138 so that product made with the master or shim tool after its failure can be removed from inventory.

Figure 5:
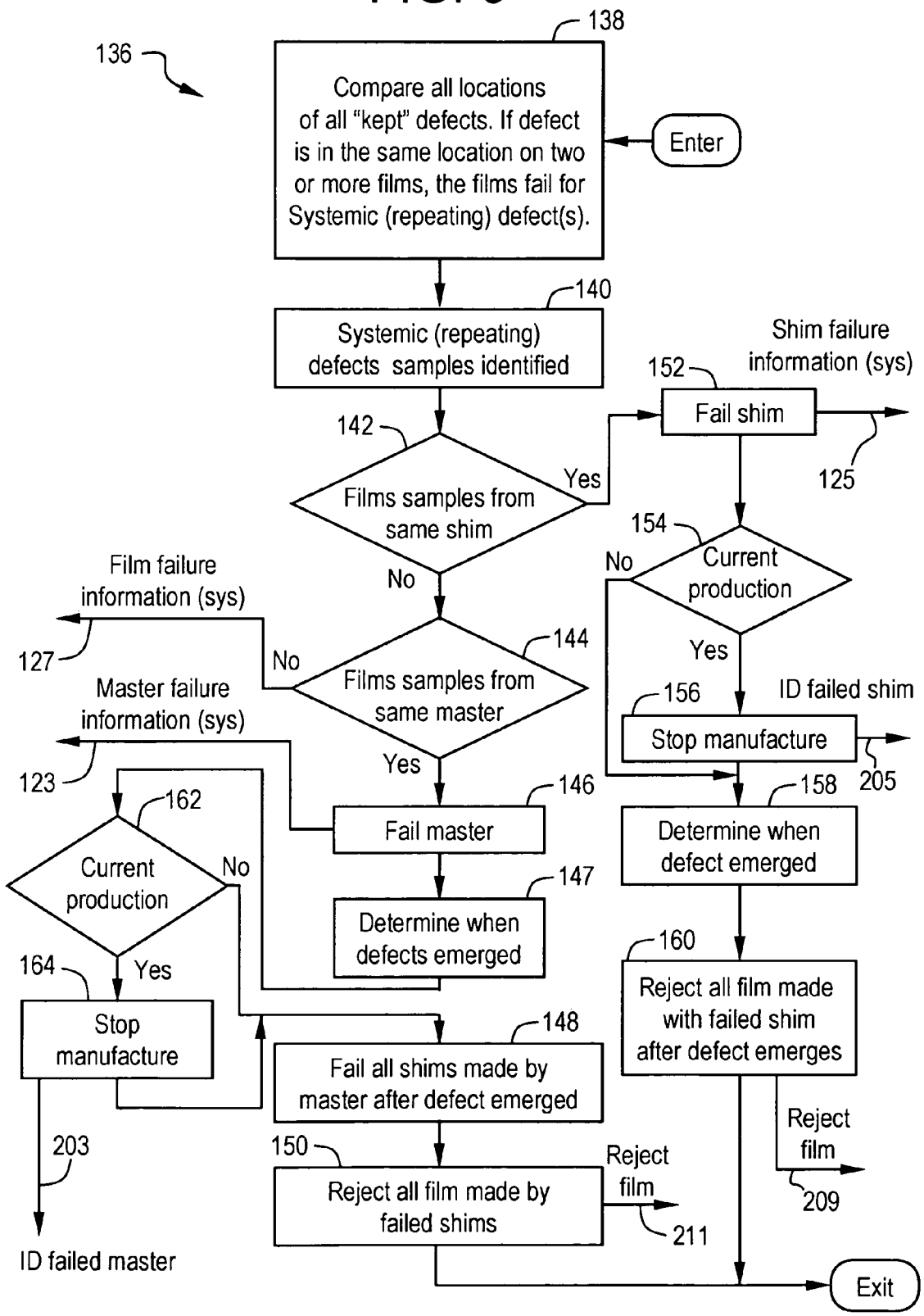
FIG. 5 is a detailed system flow diagram of the process steps for detecting and correcting systemic defects illustrated in FIG. 1.

FIG. 5 is a detailed flow diagram of Step 136 detailing the detection, classification and correction of systemic defects in the display films. Systemic defects are generally those defects or errors that repeat or are found in more than one product sample and are likely caused by prior sub-processes or sub-products used in previous steps of the overall manufacturing process. There are many algorithms to identify systemic failures and the exemplary one shown in the figure is just one. In this embodiment, the system makes a simple but elegant comparison as to the location of the defects on all failed samples. If all the defects that are retained as real defects on one sample are found in the same location as those on at least one other sample, then it is likely the defects are repeating or systemic defects. It is evident that less than all defect locations on a sample could be used to match other samples and probability functions or the like also employed to predict if such are systemic defects. It is also evident that more than two failed samples could be used for this decision. Also knowledge as to the heritage of a sample may be used in the comparisons. However, in the illustrated system, it has been found that this elegant method carried out in Step 138 of matching the defect locations of two samples works efficiently and with sufficient accuracy.

Once a systemic defect has been identified, the inspection system and defect correction procedure in Step 140 of FIG. 5 labels the samples used to make the determination as having repeating defects. The system then determines in Steps 142 and 144 their most probable origination point in the manufacturing process. If the defects samples come from the same shim tool, as tested for in Step 142, then it is likely the original or common shim tool has either worn out, was defectively made from a good master, damaged, or was made from a defective master. This path detects the worn out shim, defectively made or damaged shim and in Step 152 identifies the common shim tool as failed. Step 152 further transfers this shim failure information back to Step 130 of FIG. 3 where it can be analyzed and used to adjust the shim manufacturing process to eliminate or reduce such failures in the future. Next in Step 154, the inspection system and correction procedure determine if the shim tool identified as failed is in current production. Advantageously, the system at the first sign of shim tool failure, and likely before an automatic shut down for quality or an operator noticing the deteriorization of the quality of display films replicated from this shim, gives a directive to the film manufacturing adjustment Step 132 in FIG. 4 to remove the shim from the film manufacturing process.

Additional corrective action is taken in the next Step 158 and 160 where a determination of when the defect emerged in the shim tool is made and where a determination is made to reject all the display film made from that shim after the defect emerged, respectively. There are many ways to determine when the shim defect emerged, such as historical data on all samples made by the failed shim or an inspection of all samples made by the failed shim. A more efficacious method is to determine if there are any failed samples that were made with the failed shim in the database prior to the two or more samples that caused the failure indication. The earliest failed sample from the failed shim tool, if there are others than the two present film samples, or the earlier or the two present failed samples if there are not, is declared the time at which the failure emerged. In this manner the system corrects defects in the film inventory to a high degree of accuracy without the expensive or the time consuming method of retesting of all products made by the failed shim tool or the possibility of rejecting substantial amounts of acceptable product.

If on the other hand the defective film samples do not come from the same shim, but were made with the same master as tested for in Step 144, then it is likely the original master has either worn out, was damaged, or was defectively made. This path detects the worn out, damaged or defectively made master and in Step 146 identifies the common master as failed and transfers this master failure information back to Step 126 of FIG. 2 so that it can adjust the master manufacturing process to eliminate or reduce such failures in the future. Next in Step 162, the inspection system and defect correction procedure determines if the master tool identified as failed is in current production. Advantageously, the system at the first sign of master tool failure, and likely before an automatic shut down for quality or an operator noticing the deteriorization of the shim quality replicated from this master, gives a directive to the shim adjustment process in Step 128 in FIG. 3 to remove the master tool from the shim manufacturing process.

Additional corrective action is taken in the next Steps 147, 148, and 150. These steps are where a determination of when the master defect emerged is made in Step 147, where all the shims made from the failed master after the defect emerged are rejected in Step 148 and where all the display films made by a defective shim tool are rejected in Step 162, respectively. There are many ways to determine when the defect emerged, such as historical data on all shims made by the failed master or an inspection of all shims made by the failed master. A more efficacious method is to determine if there are any failed shim tool samples that were made with the failed master in the database prior to the two or more film samples being tested. The earliest failed shim tool sample, if there are any, or the earlier of the two or more failed film samples, if there are not, is declared the time at which the failure emerged. Subsequently, the decision is made in Step 150 to fail all film manufactured from shims made with the failed master after the defect emerged. In this manner the inspection process and defect correction process corrects defects in the film inventory to a high degree of accuracy without the expensive or the time consuming retesting of all products made by the failed master and its shim progeny, or the possibility of rejecting substantial amounts of acceptable product.

If the systemic defects are not detected as being from a particular shim or from a particular master, as indicated by the no path of Step 142 and the no path of Step 144, then the system labels them systemic defects of the film making process. Thereafter, the system transfers the film failure information about the samples to Step 134 in FIG. 4 to the analysis function for the film manufacturing process. There it is analyzed and used to adjust the film manufacturing process so as to eliminate or reduce such defects in the future.

FIG. 6 is a detailed flow chart of the inspection process of the micro-replicated film manufacturing process. It describes an integrated machine vision and visual process that provides a decision whether a film is acceptable in a more rapid and efficacious manner than before. The process flow is entered in Step 200 and implements the process step 120 of FIG. 4. Each film sample N, one out of many of the Y display films manufactured, is inspected by a machine vision system a first time in Step 200 and the defects from that machine scan recorded and identified as to selected defect categories for size, type and location. In the next Step 202, the film is cleaned with a high pressure ionizing air blast from the edge of an ionizing air knife. This removes static charge from the film; removes dust or other removable debris from the film, or at least moves it to a different location. The film sample is then machined scanned a second time in Step 204 and the defects found in that scan identified as to the selected categories of size, type and location.

To make the process as efficient as possible, these scans can be made at relatively high speeds and relatively low resolution and are mainly for identifying as many defects as possible and as quickly as possible. The information recorded for the first scan and that recorded for the second scan is now compared in Step 206. If a defect is in the same location in both scans, then it may be a true defect and is retained for further processing. Those defects that do not appear in the second machine scan, or those which only appear after cleaning are discarded as false positives and are likely just dust particles or other debris.

The machine vision system then is increased in resolution and slowed in scan speed and zooms in on individual defects to produce a third scan of every remaining defect only more thoroughly in Step 208. In this step, every remaining defect is judged against product criterion for its size, location and type. Those defects that are within product specifications and are judged acceptable are again discarded. Those defects that fail the product specification criteria are retained for further inspection. A human inspector accomplishes the next step 210 by visual inspection. The visual confirmation of a defects after many false positives have been located and discarded by the machine vision scans improves the overall efficiency of the process because the slow but discerning visual inspection is used only to confirm that what the machine vision system found were an actual defect.

Any recorded defect still remaining that cannot be visually confirmed or that is acceptable to the visual inspection is discarded in Step 210. Because many of these display films will be used with a diffuser and will be inspected only on that basis, in Step 211 the inspector will place the sample in contact with a diffuser in the way it will be used commercially and visually inspect the remaining defects to see if any more can be discarded. The sample of film is now judged on a pass/fail basis in Step 212, where if all of the noted defects have been discarded so that there are not any left, the display film sample will pass on to inventory in Step 214. If any defect still remains, the sample of display film is failed in Step 212 and the film failure information on the identity of those defects fed back to Step 134 of FIG. 4. The film failure information is also sent to the systemic defect detector step 136 to be processed.

With respect now to FIGS. 7A and 7B illustrating Table A, there is shown an experimental verification for the correlation of defect information between the process steps of a manufacturing technique and the advantage of the integration of machine vision and visual inspection data. In the manufacturing process described, a particular shim M1-14-2 was used to manufacture a number of film samples. The identification system was used to trace the shim back to the master tool, so that this shim is the second copy of the fourteenth copy of the master M1. This demonstration shows that defects found in the inspection of the shim actually translate into defects that will be found in the inspection of the display films. Similarly, it shows the advantage of correlating machine vision inspections with visual inspections, because the final product, a display film for a LCD backlight, will be visually inspected by the customer. The table illustrates that a plurality of defects which were first found on the shim tool with a machine vision system were given a number in column 1. The machine vision location of each defect was also recorded in the second and third columns and the size of the defect recorded in columns 5 and 6.

Of the twenty original defects, four were deemed acceptable by the classification rules of the machine vision system. Of the remaining sixteen defects, eleven were judged to be actual defects and were confirmed by the visual inspection that they would be present on display film made with this shim tool. There were also five false positive defects identified, i.e. those defects which were identified by the machine vision system for the shim tool but were not visible on the display film (four) or were visible on the display film but were deemed acceptable (one). With this information as to which defects were visible through the visual inspection of the display film, the shim tool inspection protocol was modified to exclude defects whose size, as defined by (length+width)/2, was less than 0.125 mm. With this feedback and correction to the shim tool inspection process, only three of the original false positives for the shim tool inspection would remain.

Figure 8:
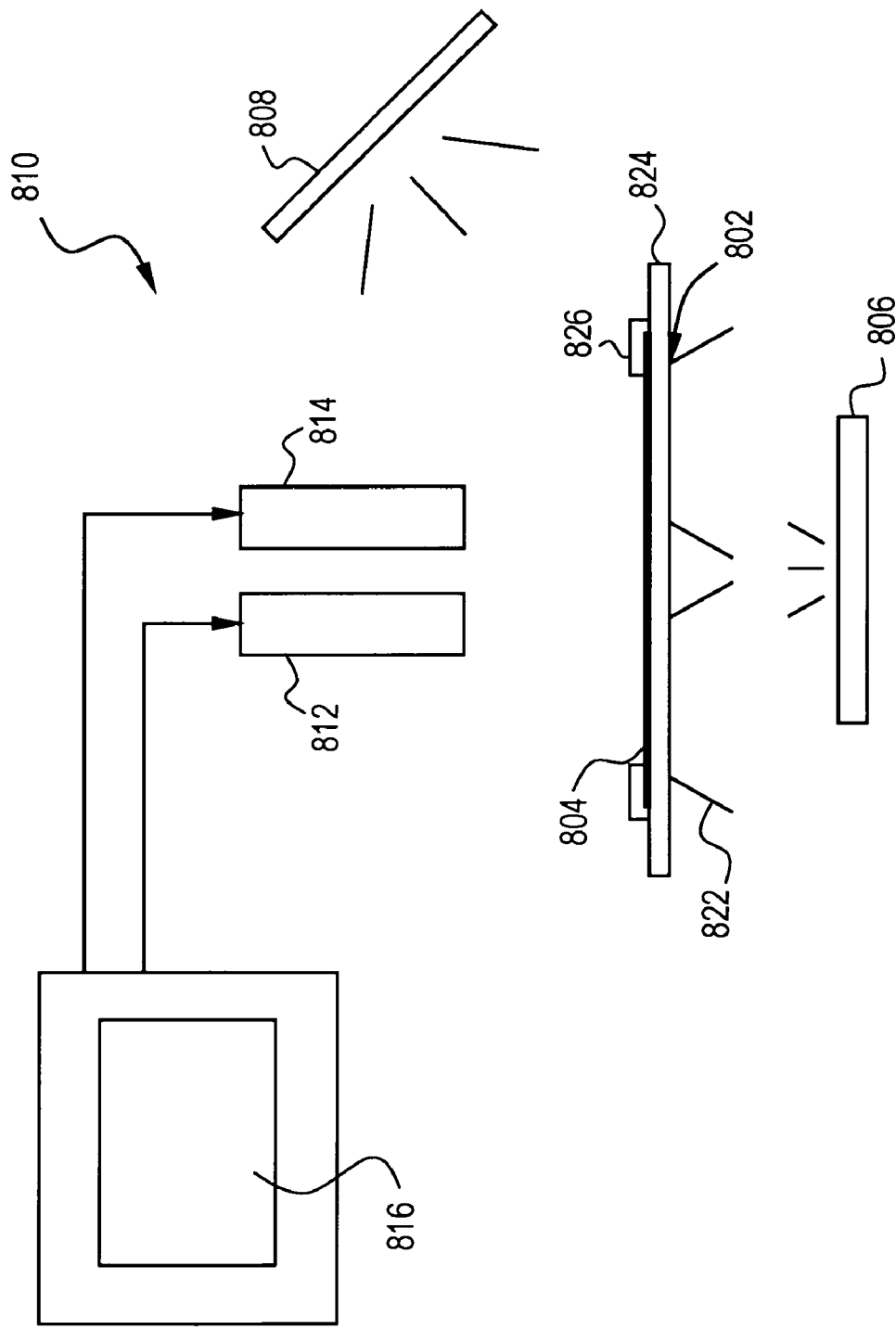
FIG. 8 is a hardware block diagram of an automated machine vision system which can be used to advantage in the inspection processes illustrated in FIG. 3 and FIG. 6.

FIG. 8 illustrates an exemplary automated or machine vision system 810 which can be used in the inspection process 116 for the shim or in the inspection process 120 for the display film. The machine vision system 810 comprises a sample holder 802 upon which a shim or display film sample 804 to be inspected is placed. The display film may be held in the sample holder 802 by a fixture (not shown). The figure shows a sample holder 802 comprising a metal fixture 822, a glass plate 824 for placing the display film or shim sample on and alignment guides 826 for aligning the display film or electroform sample. Preferably, a transmissive illumination source 806 is placed below the sample holder 802 while a reflective illumination source 808 is placed above the sample holder 802. The sources 806 and 808 are both used to illuminate the sample in order to examine it for defects. The illumination arrangement can be used to create different backgrounds against which the defects are contrasted. The machine vision system further comprises a low resolution digital camera 812 and a high resolution digital camera 814 that are used to capture images of the samples and transmit them to a computerized control system 816. If the cameras are analog, an analog to digital converter may be used between the image capture and the storage of the image in the computerized control system 816.

Upon placing the sample in the holder 802, an image is first acquired by scanning the sample with the low resolution camera 812. This is generally done at a fairly high speed and is usually for defect identification purposes. Later, when a defect has been identified, the high resolution camera 814 which can have multiple lenses can zoom in on the identified defect for classification and further study at a lower speed. Since the area of the field of view of the cameras 812 and 814 are usually less than the area inspected for a sample, the cameras may make multiple scans or passes across the sample in order to image the entire area of interest of the sample being inspected. Following the capture of the image, the machine vision system 810 uses an automated program to accomplish a series of process actions that result in the identification, removal and classification of a number of defects for the sample. Initially, the alignment of the sample may be determined and areas outside of the useful area eliminated from the analysis.

There are a variety of defects that occur in the shim tool and display film samples. With regard to the display film, there are two types of typical defects namely integral and removable defects. Integral defects are those caused by defects inherent in the shim from which it was made. Such integral defects are caused by physical damage due to wear, mishandling, or an error in manufacture that is present in the on the surface of the shim. These defects are generally termed scratches, dashes or separation marks. Removable defects are superficial defects which are often called stains, dust, spiders, blue spots or whiskers. These defects are caused by the presence of removable debris on the sample. If either removable or integral defects are left on the shim tool, they will generally translate into defects in the display film samples.

Defect determination in the machine vision system 810 is made by a series of classification rules stored in the computerized control 816. In general, identification and classification may be made on the basis of intensity and size of the recorded defect. Defects that are of higher intensity than a threshold and of larger size than an area threshold are identified as a defect and stored for further analysis. Defects that have a size or area below the threshold are ignored and not counted as defects. In this manner small defects and non-defective regions are ignored by the identification process. In addition, morphological operators may be used to merge adjacent defects that appear to be multiple into one similar defect. For example, during manufacturing some of the edges of the prisms on the surface of a display film may get scratched thereby producing defects. Such prism damage defects appear as multiple bright spots very close together. The classification rules may merge these adjacent spots together so this defect is only counted once. Similarly, it is possible to get a cluster of very small defects together. Each defect by itself would be too small to be counted and would normally be removed from the image as part of the background. However, since the defects are clustered, the collection of them may be noticeable and should be recorded as one defect.

The classification rules may also divide the defects according to size where the categories of large, medium and small are used to separate the defects so different algorithms can be used to analyze them. Following the classification of the defects, their characteristics are stored for further analysis and processing. Information on the physical characteristics of the defects are their size, location, dimensions, aspect ratio, orientation, distance from the surface or the like. Moreover, each defect may optionally be stored as an image by cropping a region of interest around each defect and saving the image.

Further, for the machine vision system 810 shown, the inspection system has the capability to feedback information to an analysis program which then adjusts the operating parameters of the system or modifies the identification and classification rules of the system. For example, if the machine vision 810 is finding to many false defects, then the classification rules for those defects and the operating parameters including scan speed and resolution may be changed to exclude such possible defects in the future. If the machine vision 810 is not finding defects which show up later in the display film, then the classification rules for those defects and the operating parameters including scan speed and resolution may be changed to include such possible defects in the future.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Further, the processes described are not necessarily to be performed only in the sequence illustrated or each step only at the time indicated. Therefore, it is intended that the invention not be limited to the particular embodiment disclosed as the best mode contemplated for carrying out this invention, but that the invention will include all embodiments falling within the scope of the appended claims.

What is claimed is:

1. A method of inspection and defect correction for microreplicated display films comprising the steps of:
   a.) manufacturing a master;
   b.) inspecting said master for performance and appearance and determining whether the master is acceptable or not acceptable;
   c.) proceeding to step g, if said master is found to be acceptable, else continuing to step d;
   d.) storing master failure information related to why the master was not acceptable;
   e.) adjusting the master manufacturing process based upon the master failure information;
   f.) proceeding to step a;
   g.) manufacturing at least one shim from said acceptable master;
   h.) inspecting for performance and appearance at least one of said shim and determining whether the shim is acceptable or not acceptable;
   i.) proceeding to step m, if said shim is found to be acceptable, else continuing to step j;
   j.) storing shim failure information related to why the shim was not acceptable;
   k.) adjusting the shim manufacturing process based upon the shim failure information;
   l.) proceeding to step g;
   m.) manufacturing at least one display film from at least one of said acceptable shim;
   n.) inspecting for performance and appearance said at least one display film and determining whether the display film is acceptable or not acceptable;
   o.) proceeding to step s, if said at least one display film is found to be acceptable, else continuing to step p;
   p.) storing the film failure information related to why the display film was not acceptable;

q.) adjusting the film manufacturing process based upon the film failure information;

r.) proceeding to step m;

s.) determining from a plurality of film failure information whether there is a systemic defect occurring in the manufacturing of said display films, and wherein the inspection and defect correction further comprises of analyzing said systematic defects and determining whether said systematic defects are occurring in the step of manufacturing the display film, the step of manufacturing shim, or the manufacturing of the master; and then adjusting at least one of said steps of manufacturing the display film, the step of manufacturing the shim, or the manufacturing the master based upon said determination.

2. A method of inspection and defect correction for microreplicated films as set forth in claim 1 wherein the step of adjusting at least one of the steps of manufacturing the display film, the step of manufacturing the shim, or the step of manufacturing the master based upon said determination further comprises:

adjusting the step of manufacturing the display film based upon a systemic film failure determination.

3. A method of inspection and defect correction for microreplicated films as set forth in claim 2 wherein the step of adjusting the manufacturing the display film based upon a systemic film failure determination further includes:

adjusting the manufacturing the display film based upon the feed back of systemic film failure information.

4. A method of inspection and defect correction for microreplicated films as set forth in claim 1 wherein the step of adjusting at least one of the step of manufacturing the display film, the step of manufacturing the shim, or the step of manufacturing the master based upon said determination further comprises:

adjusting the step of manufacturing the shim based upon a systemic shim failure determination.

5. A method of inspection and defect correction for microreplicated films as set forth in claim 4 wherein the step of adjusting the manufacturing the shims based upon a systemic shim failure determination further includes:

adjusting the manufacturing the shim based upon the feed back of systemic shim failure information.

6. A method of inspection and defect correction for microreplicated films as set forth in claim 1 wherein the step of adjusting at least one of the step of manufacturing the display film, the step of manufacturing the shim, or the step of manufacturing the master based upon said determination further comprises:

adjusting the step of manufacturing the master based upon a systemic master failure determination.

7. A method of inspection and defect correction for microreplicated films as set forth in claim 2 wherein the step of adjusting the manufacturing the master based upon a systemic master failure determination further includes:

adjusting the manufacturing the film based upon the feed back of systemic master failure information.

8. A method of inspection and defect correction for microreplicated films as set forth in claim 1 further including the steps of:

associating with each display film, the shim from which it was manufactured; and associating with each shim, the master from which it was manufactured.

9. A method of inspection and defect correction for microreplicated films as set forth in claim 8 further comprising the steps of:

analyzing said systemic defects;

determining whether said systemic defects are occurring in the step of manufacturing the display film, the step of manufacturing the shim, or the step of manufacturing the master;

determining the identity of a shim from which systemic defects have occurred;

determining the identity of a master from which systemic defects have occurred; and adjusting at least one of said step of manufacturing the display film, the step of manufacturing the shim, or the step of manufacturing the master based upon said determination of the step of manufacturing in which such systemic defects have occurred and the determination of the identity of the shim or master from which systemic defects have occurred.

10. A method of inspection and defect correction for microreplicated films as set forth in claim 9 wherein said step of adjusting further comprises:

adjusting said step of manufacturing the display film by eliminating any shims used in manufacturing that have been identified as causing systemic defects.

11. A method of inspection and defect correction for microreplicated films as set forth in claim 9 wherein said step of adjusting further comprises:

adjusting said step of manufacturing the shim by eliminating any master used in manufacturing that has been identified as causing systemic defects.

12. A method of inspection and defect correction for microreplicated films as set forth in claim 9 which further includes the steps of:

placing the display film in inventory.

13. A method of inspection and defect correction for microreplicated films as set forth in claim 12, which further includes the steps of:

rejecting from said inventory any display film associated with any shim that has been identified as causing systemic defects.

14. A method of inspection and defect correction for microreplicated films as set forth in claim 13, which further includes the steps of:

identifying a failure time when a shim began causing systemic defects;

rejecting from said inventory any display film associated with said identified shim after that failure time.

15. A method of inspection and defect correction for microreplicated films as set forth in claim 12, which further includes the steps of:

rejecting from said inventory any display film associated with any master, which has been identified as causing systemic defects.

16. A method of inspection and defect correction for microreplicated films as set forth in claim 15, which further includes the steps of:

identifying a failure time when said master began causing systemic defects;

rejecting from said inventory any display film associated with said identified master after that failure time.

* * * * *